United States Patent [19]

Roy

[11] Patent Number: 5,376,771
[45] Date of Patent: Dec. 27, 1994

[54] HIGH SPEED PROCESS FOR PREPARING ORIFICES IN PHARMACEUTICAL DOSAGE FORMS

[75] Inventor: Stephen Roy, Westfield, Mass.

[73] Assignee: Merck & Co., Inc., Rahway, N.J.

[21] Appl. No.: 909,892

[22] Filed: Jul. 7, 1992

[51] Int. Cl.⁵ .............................................. B23K 26/00
[52] U.S. Cl. ............................ 219/121.71; 219/121.82
[58] Field of Search ............. 219/121.7, 121.71, 121.82

[56] References Cited

U.S. PATENT DOCUMENTS

| | | | |
|---|---|---|---|
| 3,620,759 | 11/1971 | Maddox | 99/78 |
| 3,657,510 | 4/1972 | Rothrock | 219/121.61 |
| 3,823,816 | 7/1974 | Controulis et al. | 206/438 X |
| 4,063,064 | 12/1977 | Saunders et al. | 219/121.7 |
| 4,088,864 | 5/1978 | Theeuwes et al. | 219/121.71 |
| 4,524,785 | 6/1985 | Seragnoli et al. | 219/121.7 X |
| 4,900,876 | 2/1990 | Bushman et al. | 119/106 |
| 4,901,674 | 2/1990 | Bushman et al. | 119/106 |
| 4,906,813 | 3/1990 | Gajdos | 219/121.68 |
| 5,049,721 | 9/1991 | Parnas et al. | 219/121.68 |

OTHER PUBLICATIONS

N. K. Jain and S. U. Naik, "The in vitro and in vivo Performance of a Novel Slow Release Capsule–Compared with a Conventional Capsule", Drug Development and Industrial Pharmacy, 15(1), 117–132 (1989).

*Primary Examiner*—C. L. Albritton
*Attorney, Agent, or Firm*—Francis P. Bigley; Mark R. Daniel

[57] ABSTRACT

A laser drilling process capable of producing a plurality of holes in a pharmaceutical dosage form, at high speed, is presented. The process utilizes a digital laser marking system (DigiMark ™ variable marking system) to produce an unlimited number of holes through the surface or coating of a dosage form, at rates up to 100,000 units or more per hour.

18 Claims, 2 Drawing Sheets

HIGH SPEED PROCESS FOR PREPARING ORIFICES IN PHARMACEUTICAL DOSAGE FORMS

BACKGROUND OF THE INVENTION

There is a need within the pharmaceutical industry to produce an opening in the surface of many types of dosage forms. For example, certain controlled release devices rely on an opening which extends from outside the device, through an outer coating or housing and into the core of the device, as a means of releasing material stored within the core to the environment of use.

Often these controlled release devices rely on osmotic pressure, diffusion or surface hydration to deliver the contents of the core through the opening.

U.S. Pat. No. 4,088,864 reported the use of a laser to produce outlet passage-ways in the walls of pills which dispense their contents osmotically. This technique comprised moving the pills in succession along a predetermined path at a predetermined velocity; tracking the moving pills seriatim with a laser of a wavelength which is absorbable by the walls. The laser beam dimensions at the wall, the laser power and the firing duration were such as to cause the laser beam to heat and pierce the wall and produce an outlet passageway 4 to 2000 microns in diameter through the wall and into the device core.

There is further a need to produce dosage forms containing multiple holes through the dosage form and into the core of the dosage form. Application Ser. No. 07/815,304, filed Dec. 28, 1991, for example, relies in part on multiple holes drilled through a water impermeable membrane. The holes expose multiple portions of the dosage form core to the environment of use, allowing for delivery of the drug stored within the core.

Jain, N. K. and Naik S. U., J. Pharm Sci., 73, 1806–1811 (1984), have reported on the use of a laser to drill holes in capsules. To vary the number of pores, the capsule was mounted on a linear drive and moved at a speed of 2 mm/sec. By changing the laser frequency and keeping the power and pulse width constant 25 to 100 pores were drilled on the body of the capsule shell.

Technology required to produce multiple patterns of openings through the dosage form shell or coating without repositioning of the dosage form has previously not been available. A process which provides for rapid throughput of dosage forms, capable of providing such a pattern of openings, without such manipulation is desirable.

Recently, laser systems which employ a linear array of individual laser tubes have been developed. These systems allow the user to pulse only those lasers needed so as to produce a linear array of laser beams. In U.S. Pat. No. 5,049,721, such a system was used to provided markings in an outer jacket of repetitively spaced sections along the length of a moving cable. As the cable was moved along, the lasers were pulsed, via a computer program, to produce the letters and symbols.

Applicants have found a novel use for this technology in the chemical delivery field, in that multiple arrays of holes can be drilled in dosage form devices more rapidly and precisely than heretofore thought possible.

SUMMARY OF THE INVENTION

The present invention is directed to a novel process for producing a plurality of apertures in a chemical dosage form using a digital laser marking system. The chemical dosage form is conveyed to the laser stage using any conventional means. Once in position, any of the plurality of tubes of the digital laser marking system can be pulsed individually or in parallel. The pulse width, the composition of the dosage form and the speed which the tablet travels through the stage, determines the depth through which the laser burns and the shape of the aperture. Since the laser tubes are individually controlled, a desired pattern of apertures can be produced on the dosage form. By varying the internal stroke time, a two dimensional array of apertures may be reproducibly drilled on the dosage forms. Using mirrors and other optical devices, multiple faces of the dosage form may be drilled simultaneously.

DETAILED DESCRIPTION OF THE DRAWINGS

Figure 1:
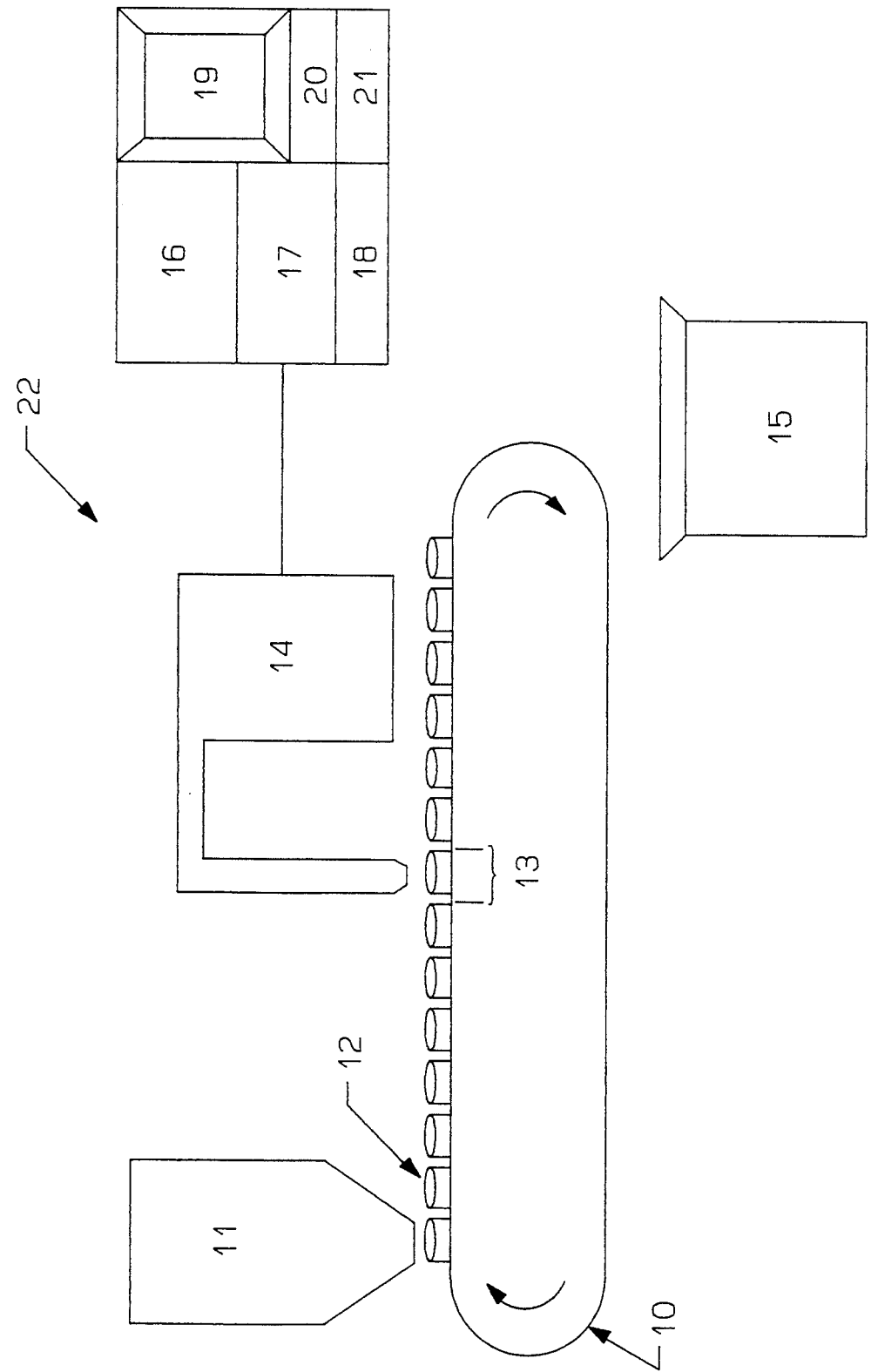
FIG. 1, is a side view of the process wherein dosage forms are continuously moved through the stage below the digital laser marking system.

In FIG. 1, dosage forms (13) are delivered to a moving conveyer system (10) from a storage container (11). The moving conveyer system (10) transports the dosage form into and out of the laser stage (13) of a digital laser marking system (14). The apertured dosage forms are collected in a final storage container (15).

U.S. Pat. No. 4,720,618 and U.S. Pat. No. 4,727,235 teach the laser marker (22) of FIG. 1 and hereby are incorporated by reference. The laser marker includes a computer (16), a monitor (19) with a keyboard (20), a laser interface circuit (17), seven radio frequency amplifiers (18), a direct current power supply (21) and a laser head (14) with a beam delivery tube and a lens. The laser head (14) includes seven carbon dioxide lasers which are excited by radio frequency energy at a frequency of 27 mega hertz to a nominal power of 20 watts. The output beams of the seven lasers are directed through the beam delivery tube via mirrors onto the lens which focuses the output beams onto a drilling area. The output of the seven carbon dioxide lasers are focused by the lens to form a seven dot-high vertical column of beams. Since the surface of the dosage form (12) moves transversely with respect to the vertical column it is possible to create a 7 by n dot array, (where n is the number of columns of dots in the array). Designs may be generated by selectively controlling each laser and the velocity of the dosage form through the laser stage (13). The keyboard (20) of the monitor (19) permits the operator to communicate with the computer (16) in order to enter data and alter the operation of the laser interface circuit (17). The radio frequency energy for exciting the lasers is generated by the radio frequency amplifiers (18) which are located in a control console. There is one radio frequency amplifier (18) for each laser. The radio frequency amplifiers (18) are controlled by digital signals from the computer (16) via the laser interface circuit (17). Each laser is controllable by a separate signal which turns the laser on or off depending on the desired aperture array.

Figure 3:
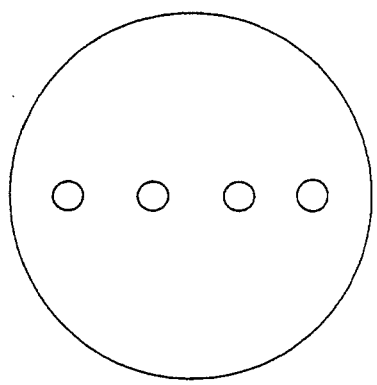
FIG. 3, is a plan view of an apertured dosage form containing four circular apertures.
Figure 4:
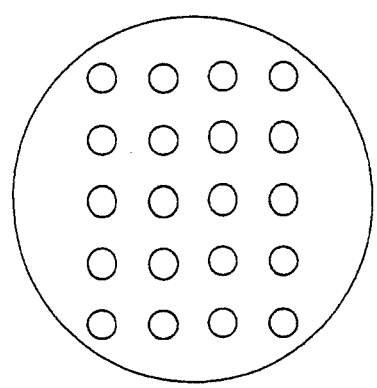
FIG. 4, is a plan view of an apertured dosage form containing a 4×5 array of circular apertures.

Referring to FIG. 3 in conjunction with FIG. 1, the apertures (30) are a plurality of drilled openings which pierce the outer surface of the dosage form. If four of the carbon dioxide lasers are pulsed once while a dosage form is within the laser stage (13) a single linear array of four apertures appear in the dosage form. However, if four of the carbon dioxide lasers are pulsed five times while the dosage form moves through the laser stage (13) then the dosage form depicted in FIG. 4 results, containing a 4×5 array of apertures.

Figure 5:
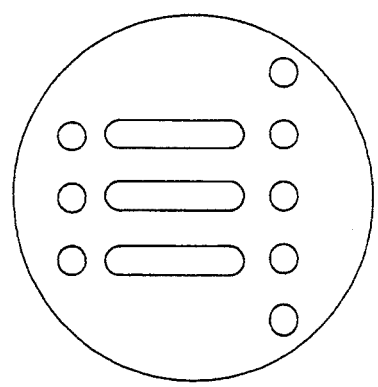
FIG. 5, is a plan view of an apertured dosage form containing three different linear arrays of apertures.

The speed with which the dosage form moves through the laser stage and the pulse width determine the shape of the aperture. As FIG. 5 shows, near circular apertures (40) result from short pulse width and reduced velocity through the laser stage (13). More elongated, oval apertures (41) may be obtained using longer pulse widths and faster movement through the laser stage (13).

Since the seven carbon dioxide lasers can be independently pulsed, arrays such as that depicted in FIG. 5 can result. That is, combinations of different types of apertures may be produced on the same dosage form.

The distance between the linear arrays is a function of the internal stroke time of the laser and the velocity of the dosage form through the laser stage. Shorter internal stroke times or faster dosage form velocity or both result in reduced distance between the linear arrays.

The depth of the apertures in the dosage form is a function of the pulse width, velocity and the composition of the dosage form. Aperture depth of from about 20 microns to about 1 cm may be required depending upon the application.

In alternative embodiments of the present invention, other laser marking systems may be used to produce the apertures in the dosage form. The laser marker of the preferred embodiment includes seven carbon dioxide lasers. U.S. Pat. No. 4,636,043, teaches another laser marker which utilizes a laser scanner to mark items. U.S. Pat. No. 4,024,545, teaches yet another laser marker for inscribing markings, such as alphanumeric characters and symbols, in the outer surface layer of an article in accordance with predetermined information. Other lasers, including, but not being limited to, an argon laser, another carbon dioxide laser, a neodymium:YAG laser, an erbium:YAG laser, and an excimer laser, may be used in each of these laser markers so long as the laser marker is able to produce apertures in the dosage form (12).

From the foregoing, it can be seen that a laser marking apparatus which provides a array of apertures in a moving dosage form has been described.

It should be noted that the sketches are not drawn to scale and that distance between the Figures are not to be considered significant.

DESCRIPTION OF THE INVENTION

The invention concerns a novel process for producing a dosage form having a plurality of apertures in its outside surface, using a digital laser marking system focused at a laser stage, the steps comprising:
 (a) moving the dosage form into the laser stage of the digital laser marking system;
 (b) pulsing the digital laser marking system to energize those laser tubes needed to drill the desired apertures along a linear array on the dosage form;
 (c) moving the dosage form forward at the laser stage and pulsing the digital laser marking system to produce an additional linear array of apertures as required;
 (d) removing the dosage form from the laser stage.

By "dosage form" is meant any device capable of delivering a chemical which requires a plurality of apertures through which the chemical may move into the environment of use. The environment of use is not limited. It may be of a biological nature, for example pharmaceutical drug delivery, or industrial use such as water or air treatment, or any other area in need of delivery of a chemical through a plurality of apertures. The term "dosage form" further includes but is not limited to items such as coated or uncoated tablets, capsules, lozenges, boluses, pills, wafers, disks, expandable devices, patches, suppositories, collars, pellets, controlled release devices, slow release devices, room freshener devices, water treatment delivery devices, and other chemical delivery devices.

By "laser stage" is meant the area accessible to the laser beams where drilling may occur. This area may be directly below the laser tubes or if suitable optics are utilized my be remotely located from the bottom of the laser tubes.

By "apertures" is meant holes or openings starting at the surface of the dosage form and extending into the dosage form to a predetermined depth within the dosage form. Alternatively, the apertures may go completely through the dosage form. The apertures may pierce the coating of a dosage form thus exposing the interior of the dosage form to the environment of use. Additionally, the apertures may provide an exit means for the chemical stored inside a dosage form to be expelled under osmotic pressure, diffusion or surface hydration.

The apertures may be arrayed closely so as to produce perforations which define an area of the dosage form which is to be discarded prior to use or expelled during use. Any number of apertures may be contained within the array. When boluses and other large dosage forms are prepared, m×n array containing from 1 to 1000 or more apertures for each member of the array may be needed. Thus, it would not be outside this invention for a dosage form to contain 1000 columns of apertures each containing 1000 apertures (i.e. m=1000 and n=1000). For most larger dosage forms, from 5 to 1000 apertures are drilled in one or more faces of the dosage form.

When other smaller dosage forms are prepared, m×n arrays containing from 10 to 50 apertures may be required. Thus, it would be within this invention for a dosage form to contain 5 columns of 10 apertures each. (i.e. m=5 and n=10) Further, the apertures may be arrayed in a manner which produces a pattern which identifies the dosage form prior to or during use.

The digital laser marking system may be used either alone or in conjunction with a printing means to inscribe alpha-numeric characters or other symbols on the dosage form using technology such as that described in U.S. Pat. No. 5,049,721 which is hereby incorporated by reference, in such a manner that the characters mask or hide the apertures. In addition, the apertures may be arrayed to produce a design, spell out a code, trademark or other symbol.

The number and size of the apertures is determined by the end use of the dosage form. For example, such apertures could be used to limit or enhance the delivery rate of the chemical to the environment of use.

In the pharmaceutical field, the dosage form may consist of a tablet or other drug delivery device. The drug delivery device may be coated or uncoated. Uncoated tablets may contain apertures in order to assure rapid disintegration of the tablet or to produce incursions which help in breaking the tablet. Coated tablets may contain apertures to assist in entry of fluid from the environment of use, allow for passage of drug from the core of the tablet to the environment or to define the amount of core area exposed to the environment.

The dosage form may be a core which comprises a polymer which forms gelatinous microscopic particles upon hydration and a medicament, the core being completely coated with a water insoluble and water impermeable coating. This process for producing a plurality of apertures using a digital laser marking system may then be used to drill a predetermined number of apertures into the surface of the dosage form. If the dosage form has distinct faces, apertures may be drilled in all of the faces, either sequentially or simultaneously. In a system of this type, the apertures provide access to the solution which makes up the environment of use. The solution hydrates the polymer at the exposed surfaces. The polymer forms gelatinous microscopic particles which move from the tablet into the environment of use, carrying with them the active ingredient.

The preferred digital laser marking system has been previously described. This system is commercially available under the name DIGIMARK TM. The seven carbon dioxide laser tubes can be individually pulsed and produce a 7×n matrix on the dosage form. The length of time that the laser is pulsed is referred to as the pulse width. This time is measured in microseconds. The depth of each aperture is determined by the operational wattage, the characteristics of the dosage form surface, the velocity at which the dosage form travels through the laser stage and the pulse width. Pulse widths of from about 1 microsecond to about 10,000 microsecond may be useful in this process.

The cycle time between pulses is referred to as the internal stroke time. This is the amount of time from the start of one pulse to the start of the next. As indicated earlier, internal stroke time and dosage form velocity determine the distance between the linear arrays of apertures. Internal stroke times of from about 1 microsecond to about 20,000 microsecond may be useful for generating apertures in dosage forms.

The energy developed by the laser may range from about 5 to about 1000 watts. The wavelength of a carbon dioxide laser is ablut 10.6 microns.

By "pulsing the digital laser marking system" is meant that a signal is sent to any or all of the lasers to energize the laser beam. The pulse width may vary from about 1 usec to about 10,000 microseconds When the pulse width is relatively short and the dosage form velocity through the laser stage is relatively slow, a more circular aperture will result. The diameter of the apertures contemplated by this invention ranges from about 100 um to about 2000 um. If the pulse width is relatively long and the dosage form velocity through the laser stage relatively fast, a more oval shaped aperture results. The length of the oval shaped aperture may extend from one end of the dosage form to the other. However, in general, the length ranges from about 20 microns to about 1 cm. The width of the oval shaped apertures ranges from about 20 microns to about 2000 microns.

The dosage forms may be moved onto the laser stage by any conventional or non-conventional means, including manual incursion and removal. In practice, a conveyer system may be employed to move up to about 100,000 dosage forms per hour through the laser stage. The dosage form may be moved to the laser stage quickly and then more slowly move across the stage to produce the desired array of apertures. Further, the dosage form may be rotated, inverted or otherwise maneuvered to allow for the production of apertures on all sides of the dosage form.

In another embodiment of this technology, the laser beams may be split using mirrors or other optical devices so that more than one side of the dosage form may be drilled simultaneously.

EXAMPLES

Example 1

Tablets cores containing lovastatin, CARBOPOL ® 974P, trisodium citrate and lactose in ratios of 3:2:2:2 were prepared by compression using ¼ inch standard concave punches. The tablets were coated to a thickness of 100 microns with a coating composition comprising cellulose acetate butyrate and triethyl citrate, using a Freund ® Model MCT-Mini H-Coater (8-inch pan).

Figure 2:
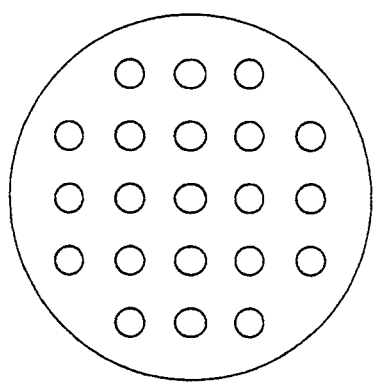
FIG. 2, is a plan view of an apertured dosage form containing 21 apertures.

Twenty-one apertures were drilled in each face of the coated tablets, as shown in FIG. 2, using a DIGIMARK TM digital laser marking system at four pulse width settings of 1000, 1500, 2000 and 2500 micro seconds, at a surface feed rate of 15 feet per minute. This feed rate corresponds to approximately 32,400 tablets per hour if the tablets were arranged three to an inch and both faces of the tablet were drilled simultaneously. The approximate hole size, as measured by microscopic imaging using an Analytical Imaging Concepts IM4000, is reported in Table I.

As the results indicate, the hole size increased with an increase in the pulse width. The grid of holes was centered on the tablet face and occupied an area less than half that of the tablet face. The distance between the rows and columns of holes was approximately one hole diameter.

In vitro release tests were carried out at 37° C. using USP Apparatus II in pH 7.4 phosphate buffer containing 0.4% sodium dodecyl sulfate at 50 rpm. The drug released was monitored by flow-through UV spectrophotometry. Tablets marked with all but the lowest pulse width (1000 microseconds) were observed to release lovastatin at a similar rate with no appreciable lag time.

TABLE I

Release Rate of Laser Marked (21 holes/face) Tablets

| Pulse Width | Hole Size | Cumulative Percent Lovastatin Released | | |
|---|---|---|---|---|
| | | 5 hr | 10 hr | 15 hr |
| 2500 | 396 +/− 19 um | 30, 28 | 56, 52 | 73, 70 |
| 2000 | 371 +/− 30 um | 28, 27 | 53, 52 | 70, 70 |
| 1500 | 338 +/− 16 um | 27 | 51 | 68 |
| 1000 | 316 +/− 6 um | 15 | 32 | 48 |

Example 2

Twenty-four (24) apertures of 0.35 mm in diameter were drilled in each face of the coated tablets prepared for the study in Example 1 using the DIGIMARK ™ digital laser marking system. A 4×6 array was used with a pulse width of 2500 microseconds and an internal stroke of 5000 microseconds The apertures were measured as in Example 1. Release rates were studied as in Example 1. The results are shown in Table II.

TABLE II

| Release Rate of Laser Marked (24 holes/face) Tablets | | | |
|---|---|---|---|
| | Cumulative Percent Lovastatin Released | | |
| Hole Size | 5 hr | 10 hr | 15 hr |
| 0.35 mm | 52.4 ± 3.2 | 87.1 ± 1.6 | 96.5 ± 0.51 |

Example 3

Forty-two (42) apertures of 0.45 mm in diameter were drilled in a single tablet face of the coated tablets of Example 1 using the DIGIMARK ™ digital laser marking system. A 7×6 array was used with a pulse width of 4250 microseconds and an internal stroke of 8000 microseconds Measurement of the aperture size and determination of release rates were as in Example 1. The results are shown in Table III.

TABLE III

| Release Rate of Laser Marked (24 holes/face) Tablets | | | |
|---|---|---|---|
| | Cumulative Percent Lovastatin Released | | |
| Hole Size | 5 hr | 10 hr | 15 hr |
| 0.45 mm | 44.7 ± 0.4 | 72.55 ± 1.1 | 82.6 ± 0.6 |

What is claimed is:

1. A process for producing a pharmaceutical drug delivery dosage form having a plurality of apertures in its outside surface, the apertures providing an egress for a drag when the drug delivery device is placed in a biological environment of use, the process using a digital laser marking system focused at a laser stage, the steps comprising:
   (a) moving the dosage form into the laser stage of the digital laser marking system;
   (b) pulsing the digital laser marking system to energize laser tubes needed to drill the desired apertures along a linear array on the dosage form;
   (c) moving the dosage form on the laser stage and pulsing the digital laser marking system to produce an additional linear array of apertures as required;
   (d) removing the dosage form from the laser stage.

2. The process of claim 1, wherein the dosage form is designed to deliver medicament to an animal.

3. The process of claim 2, wherein the dosage form is designed to deliver medicament to a human.

4. The process of claim 1 wherein the pharmaceutical drag delivery dosage form is selected from the group consisting of tablets, capsules, lozenges, boluses, pills, wafers, disks, expandable devices, patches, suppositories, collars, pellets, controlled release devices, and slow release devices.

5. The process of claim 4 wherein the dosage form is a core covered with a water insoluble and water impermeable coating.

6. The process of claim 5 wherein the apertures are drilled through the film coating and terminate in the core of the dosage form.

7. The process of claim 6 wherein the apertures extend completely through the dosage form.

8. The process of claim 7 wherein the dosage form is moved into the working field of the digital laser marking system using a conveyer system.

9. The process of claim 8 wherein the laser tubes are pulsed for from about 1 microsecond to about 10,000 microseconds.

10. The process of claim 9 wherein the apertures are circular.

11. The process of claim 10 wherein the diameter of the circular apertures ranges from about 100 microns to about 2000 microns.

12. The process of claim 9 wherein the apertures are oval in shape.

13. The process of claim 12 wherein a cord struck across the longest dimension of the aperture ranges in length from about 20 microns to about 1 cm.

14. The process of claim 13 wherein a cord struck across the shorter dimension of the aperture ranges in length from about 20 microns to about 2000 microns.

15. The process for producing a dosage form having a plurality of apertures using the digital laser marking system of claim 1, wherein the dosage form is a film coated tablet.

16. The process for producing a dosage form having a plurality of apertures using the digital laser marking system of claim 15 wherein the dosage form comprises a core and is coated with a water insoluble coating.

17. The process for producing a dosage form having a plurality of apertures using the digital laser marking system of claim 1 wherein from 5 to 1000 apertures are drilled in each face of the dosage form.

18. The process for producing a dosage form having a plurality of apertures using the digital laser marking system of claim 17 wherein from 10 to 50 apertures are drilled in each face of the dosage form.

* * * * *